United States Patent
Sadasivan Vijayakumari et al.

(10) Patent No.: US 10,220,347 B2
(45) Date of Patent: Mar. 5, 2019

(54) PROCESS FOR RECOVERING METHANE FROM A GAS STREAM COMPRISING METHANE AND ETHYLENE

(71) Applicant: SHELL OIL COMPANY, Houston, TX (US)

(72) Inventors: Sivakumar Sadasivan Vijayakumari, Louisiana, TX (US); Charles-Edouard Sanders, Gyeongsangnam-do (KR)

(73) Assignee: SHELL OIL COMPANY, Houston, TX (US)

( * ) Notice: Subject to any disclaimer, the term of this patent is extended or adjusted under 35 U.S.C. 154(b) by 110 days.

(21) Appl. No.: 15/322,503

(22) PCT Filed: Jun. 29, 2015

(86) PCT No.: PCT/EP2015/064654
§ 371 (c)(1),
(2) Date: Dec. 28, 2016

(87) PCT Pub. No.: WO2016/001116
PCT Pub. Date: Jan. 7, 2016

(65) Prior Publication Data
US 2018/0214814 A1    Aug. 2, 2018

(30) Foreign Application Priority Data

Jun. 30, 2014  (EP) .................................. 14174887

(51) Int. Cl.
*B01D 53/02* (2006.01)
*B01D 53/047* (2006.01)
(Continued)

(52) U.S. Cl.
CPC .............. *B01D 53/047* (2013.01); *C07C 7/12* (2013.01); *C07C 7/13* (2013.01);
(Continued)

(58) Field of Classification Search
CPC ............ B01D 53/047; B01D 2253/102; B01D 2253/108; B01D 2256/245;
(Continued)

(56) References Cited

U.S. PATENT DOCUMENTS

| 5,025,108 A | 6/1991 | Cameron et al. |
| 5,113,032 A | 5/1992 | Cameron et al. |

(Continued)

FOREIGN PATENT DOCUMENTS

| CA | 1199881 | 1/1986 |
| DE | 969431 | 6/1958 |
| WO | 2012026789 | 3/2012 |

OTHER PUBLICATIONS

International Search Report dated Aug. 20, 2015 of PCT/EP2015/064654 filed Jun. 29, 2015.

*Primary Examiner* — Christopher P Jones (57) ABSTRACT

The invention relates to a process for recovering methane from a gas stream comprising methane and ethylene, comprising: a sorption step which comprises contacting the gas stream comprising methane and ethylene with a sorption agent which has a lower affinity for methane than for ethylene, wherein the gas stream comprising methane and ethylene also comprises a compound for which the sorption agent has a lower affinity than for methane and ethylene, resulting in sorption of ethylene and methane by the sorption agent and in a gas stream comprising the compound for which the sorption agent has a lower affinity than for methane and ethylene; a first desorption step which comprises desorbing part of the sorbed methane resulting in a gas stream comprising methane in an amount of 1 to 99.9% based on the amount of methane in the gas stream that is subjected to the sorption step; and a second desorption step (Continued)

which comprises desorbing sorbed compounds resulting in a gas stream comprising the desorbed compounds.

14 Claims, 2 Drawing Sheets

(51) Int. Cl.
  *C07C 7/12* (2006.01)
  *C07C 7/13* (2006.01)
(52) U.S. Cl.
  CPC .. *B01D 2253/102* (2013.01); *B01D 2253/108* (2013.01); *B01D 2256/245* (2013.01); *B01D 2257/102* (2013.01); *B01D 2257/108* (2013.01); *B01D 2257/502* (2013.01); *B01D 2257/504* (2013.01); *B01D 2257/7022* (2013.01); *Y02C 10/08* (2013.01); *Y02P 20/152* (2015.11); *Y02P 20/51* (2015.11)
(58) Field of Classification Search
  CPC ........ B01D 2257/102; B01D 2257/108; B01D 2257/502; B01D 2257/504; B01D 2257/7022; C07C 7/12; C07C 7/13
  See application file for complete search history.

(56) References Cited

U.S. PATENT DOCUMENTS

| | | |
|---|---|---|
| 8,192,709 B2 | 6/2012 | Reyes et al. |
| 2002/0007101 A1 | 1/2002 | Senetar et al. |

Fig.2

PROCESS FOR RECOVERING METHANE FROM A GAS STREAM COMPRISING METHANE AND ETHYLENE

PRIORITY CLAIM

The present application is the National Stage (§ 371) of International Application No. PCT/EP2015/064654, filed Jun. 29, 2015, which claims priority from European Patent Application No. 14174887.1, filed Jun. 30, 2014 and incorporated herein by reference.

FIELD OF THE INVENTION

The present invention relates to a process for recovering methane from a gas stream comprising methane and ethylene.

BACKGROUND OF THE INVENTION

It is known to convert methane into saturated and unsaturated, non-aromatic hydrocarbons having 2 or more carbon atoms, including ethylene, by means of a process called "Oxidative Coupling of Methane" (OCM). In this process, a gas stream comprising methane is contacted with an OCM catalyst and with an oxidant, such as oxygen or air. In such a process, two methane molecules are first coupled into one ethane molecule, which is then dehydrogenated into ethylene. Said ethane and ethylene may further react into saturated and unsaturated hydrocarbons having 3 or more carbon atoms, including propane, propylene, butane, butene, etc. Therefore, usually, the gas stream leaving an OCM process contains water, hydrogen, carbon monoxide, carbon dioxide, methane, ethane, ethylene, propane, propylene, butane, butene and saturated and unsaturated hydrocarbons having 5 or more carbon atoms. In a case where in an OCM process air is used as oxidant rather than pure oxygen, nitrogen is also present in the gas stream leaving the OCM process.

In general, the conversion that can be achieved in an OCM process is relatively low. Besides, at a higher conversion, the selectivity decreases so that it is generally desired to keep the conversion low. As a result, a relatively large amount of unconverted methane leaves the OCM process. The proportion of unconverted methane in the OCM product gas stream may be as high as 70 to 80 mol % based on the total molar amount of the gas stream. This unconverted methane has to be recovered from the desired products, such as ethylene and other saturated and unsaturated hydrocarbons having 2 or more carbon atoms, which are also present in such gas streams. Further, as mentioned above, such gas streams may also comprise compounds like nitrogen, carbon monoxide and/or hydrogen, which have a boiling point which is lower than that of methane ("light compounds").

It is known to separate the gas stream leaving an OCM process in the following way. Acid gas (mainly $CO_2$) is removed in two stages, the first stage is an aqueous monoethanolamine (MEA) absorption system, and the second stage removes final traces of $CO_2$ by scrubbing against aqueous NaOH. The $CO_2$-free gas is dried in a dessicant bed and processed in a separation train similar to that used in conventional ethylene plants. The separation sequence comprises a front end demethanizer, deethanizer, C2 splitter, depropanizer, C3 splitter, and a debutanizer. The cryogenic needs for separation are met by a propylene-ethylene cascade refrigeration system that requires ethylene refrigerant only for the demethanization stage.

Thus, it is known to separate methane from saturated and unsaturated hydrocarbons having 2 or more carbon atoms, such as ethylene, by means of cryogenic distillation in so-called "demethanizer" columns. In cryogenic distillation, a relatively high pressure (in general: 23 to 35 bar) and a relatively low (cryogenic) temperature (in general: −120 to −70° C.) are applied to effect the separation of methane. The use of cryogenic distillation following an OCM process is for example disclosed in U.S. Pat. Nos. 5,113,032 and 5,025,108.

In a case where the gas stream also comprises light compounds such as nitrogen, carbon monoxide and/or hydrogen, it is known to first separate methane and the light compounds from the higher hydrocarbons by means of cryogenic distillation as discussed above. Then the light compounds are separated from the methane which is done by means of cryogenic distillation at a relatively high pressure (in general: 23 to 35 bar) and a relatively low (cryogenic) temperature (in general: −150 to −90° C.).

An object of the invention is to provide a technically advantageous, efficient and affordable process for recovering methane from a gas stream comprising methane and ethylene, more especially in a case where such gas stream comprises a relatively high proportion of unconverted methane, and wherein such gas stream also comprises light compounds such as nitrogen, carbon monoxide and/or hydrogen. Such technically advantageous process would preferably result in a lower energy demand and/or lower capital expenditure.

SUMMARY OF THE INVENTION

Surprisingly it was found that such technically advantageous process, resulting in a lower energy demand and/or lower capital expenditure, for recovering methane from a gas stream comprising methane, ethylene and light compounds such as nitrogen, carbon monoxide and/or hydrogen may be provided by subjecting such gas stream to the following three steps:

a sorption step which comprises contacting the gas stream comprising methane and ethylene with a sorption agent which has a lower affinity for methane than for ethylene, wherein the gas stream comprising methane and ethylene also comprises a compound for which the sorption agent has a lower affinity than for methane and ethylene, resulting in sorption of ethylene and methane by the sorption agent and in a gas stream comprising the compound for which the sorption agent has a lower affinity than for methane and ethylene;

a first desorption step which comprises desorbing part of the sorbed methane resulting in a gas stream comprising methane in an amount of 1 to 99.9% based on the amount of methane in the gas stream that is subjected to the sorption step; and a second desorption step which comprises desorbing sorbed compounds resulting in a gas stream comprising the desorbed compounds.

Accordingly, the present invention relates to a process for recovering methane from a gas stream comprising methane and ethylene, comprising the above-mentioned sorption step, first desorption step and second desorption step.

DETAILED DESCRIPTION OF THE INVENTION

The gas stream that is subjected to the sorption step of the process of the present invention is a gas stream which comprises methane and ethylene. Preferably, said gas stream originates from the above-mentioned process of oxidative coupling of methane (OCM), wherein a gas stream comprising methane is contacted with an OCM catalyst and with an oxidant, such as oxygen or air, in order to convert the methane into ethylene and optionally ethane and/or saturated and unsaturated, non-aromatic hydrocarbons having 3 or more carbon atoms.

In the sorption step of the process of the present invention, the gas stream comprising methane and ethylene is contacted with a sorption agent which has a lower affinity for methane than for ethylene. In the present invention, said gas stream that is subjected to this sorption step does not only comprise methane and ethylene but it also comprises a compound for which the sorption agent has a lower affinity than for methane and ethylene. Where in the present specification reference is made to the "third component", reference is made to the compound for which the sorption agent has a lower affinity than for methane and ethylene which compound is present in the gas stream that is subjected to the sorption step.

Preferably, the compound for which the sorption agent has a lower affinity than for methane and ethylene is a light compound. Within the present specification, a "light compound" means a compound which has a boiling point which is lower than that of methane. Preferably, the compound for which the sorption agent has a lower affinity than for methane and ethylene is nitrogen, carbon monoxide, hydrogen or a mixture of two or more of these, preferably nitrogen. Further, preferably, the gas stream that is subjected to the sorption step comprises 50 to 99 mol % of methane, 1 to 50 mol % of ethylene and 0.1 to 90 mol % of the compound for which the sorption agent has a lower affinity than for methane and ethylene. The amount of nitrogen in said gas stream may be 0 to 80 mol %, for example 0.1 to 80 mol %. Nitrogen may for example be present in a case where the gas stream originates from an OCM (oxidative coupling of methane) process wherein air is used as oxidant rather than pure oxygen. The amount of carbon monoxide in said gas stream may be 0 to 20 mol %, for example 0.1 to 20 mol %. The amount of hydrogen in said gas stream may be 0 to 20 mol %, for example 0.1 to 20 mol %. Said relative amounts are based on the total amount of the gas stream.

Within the present specification, where reference is made to relative (e.g. molar) amounts of components in a gas stream, such relative amounts are to be selected such that the total amount of said gas stream does not exceed 100%.

In the sorption step of the process of the present invention, the above-mentioned gas stream comprising methane, ethylene and the compound for which the sorption agent has a lower affinity than for methane and ethylene is contacted with the sorption agent which has a lower affinity for methane than for ethylene. That is, the affinity of the sorption agent for ethylene is higher than its affinity for methane which latter affinity in turn is higher than its affinity for said third component in the gas stream. In the present invention, said sorption step results in sorption of ethylene and methane by the sorption agent and in a gas stream comprising said third component. That is to say, the gas stream resulting from the sorption step comprises said third component that is not sorbed by the sorption agent. In particular, the amount of said third component in the gas stream resulting from the sorption step is 50 to 100%, preferably 80 to 100%, based on the amount of said third component in the gas stream that is subjected to the sorption step. The latter percentage may also be referred to as "rejection" of said third component (said third component not being sorbed, but "rejected"). Such "rejection" may be varied by varying the pressure and/or the nature of the sorption agent. Consequently, the amount of said third component that is sorbed by the sorption agent in the sorption step is 0 to 50%, preferably 0 to 20%, based on the amount of said third component in the gas stream that is subjected to the sorption step.

The amount of said third component, which is the compound for which the sorption agent has a lower affinity than for methane and ethylene, in the gas stream resulting from the sorption step may be at most 100%, or at most 99%, or at most 98%, or at most 95%, based on the amount of said third component in the gas stream that is subjected to the sorption step. Further, the amount of said third component in the gas stream resulting from the sorption step may be at least 50%, or at least 70%, or at least 80%, or at least 90%, based on the amount of said third component in the gas stream that is subjected to the sorption step. Thus, said amount of said third component in the gas stream resulting from the sorption step may for example be 50 to 100% or 90 to 100%, or 50 to 95% or 90 to 95%. Consequentially, the amount of said third component that is sorbed by the sorption agent in the sorption step may be at least 1%, or at least 2%, or at least 5%, based on the amount of said third component in the gas stream that is subjected to the sorption step. Further, the amount of said third component that is sorbed by the sorption agent in the sorption step may be at most 50%, or at most 30%, or at most 20%, or at most 10%, based on the amount of said third component in the gas stream that is subjected to the sorption step. Thus, said amount of said third component that is sorbed by the sorption agent in the sorption step may for example be 1 to 50% or 1 to 10%, or 5 to 50% or 5 to 10%.

In the sorption step of the process of the present invention, a sorption agent is used. In the present specification, "sorption" means a process in which one substance (the sorption agent) takes up or holds or retains another substance by absorption, adsorption or a combination of both.

Further, said sorption agent used in the sorption step of the process of the present invention has a lower affinity for methane than for ethylene. Still further, said sorption agent has an even lower affinity for the third component in the gas stream that is subjected to the sorption step, which third component is described in the present specification as the compound for which the sorption agent has a lower affinity than for methane and ethylene and which third component, as discussed above, may for example be nitrogen, carbon monoxide, hydrogen or a mixture of two or more of these. That is, the affinity of the sorption agent for ethylene is higher than its affinity for methane which latter affinity in turn is higher than its affinity for said third component in the gas stream. The second requirement means that under the conditions applied in said sorption step, including pressure and temperature which are further defined hereinbelow, said sorption agent has a lower affinity for said third component than for methane. This implies that in the process of the present invention such sorption agent should be used in the sorption step, that the molar ratio of sorbed methane to the sorbed third component is greater than 1:1, assuming equal partial pressures for ethylene and said third component. Sorption agents suitable to be used in the present invention may be selected by comparing the extent of sorption of said third component with the extent of sorption of methane under any given temperature and pressure conditions for a variety of known sorption agents, assuming equal partial pressures for methane and said third component. Therefore, a wide range of sorption agents may be used since the only criterion in the present invention is that the sorption agent should have a lower affinity for said third component than for methane. Without any limitation, examples of suitable sorption agents are activated carbon, zeolite 13X and zeolite 5A. The foregoing also applies to the first requirement implying that the affinity of the sorption agent for ethylene should be higher than its affinity for methane.

The pressure in the sorption step of the process of the present invention may vary within wide ranges. Preferably, said pressure is higher than atmospheric pressure. More preferably, said pressure is higher than atmospheric pressure and at most 20 bar, more preferably of from 10 to 20 bar, most preferably 12 to 18 bar.

The temperature in the sorption step of the process of the present invention may also vary within wide ranges. Preferably, said temperature is in the range of from 0 to 100° C., more preferably 10 to 80° C., most preferably 25 to 50° C. Advantageously, in the present invention, said sorption step may be carried out at a non-cryogenic temperature (e.g. of from 0 to 100° C. as mentioned above).

In the present invention, it is envisaged that the gas stream resulting from the sorption step, in addition to the compound for which the sorption agent has a lower affinity than for methane and ethylene, may also comprise methane, for example in a case, wherein the feed of the gas stream to the sorption step is stopped shortly after the breakthrough of methane into the gas stream resulting from that sorption step. Said gas stream resulting from the sorption step may comprise methane in an amount of from 0.1 to 10% or 1 to 5%, based on the amount of methane in the gas stream that is subjected to the sorption step. If said gas stream also comprises methane, in addition to nitrogen, carbon monoxide and/or hydrogen, said gas stream may be used as a fuel thereby advantageously also providing energy (heat). That is to say, in such case the gas stream resulting from the sorption step is burnt resulting in the formation of carbon dioxide (from methane and any carbon monoxide) and water (from methane and any hydrogen) which may be treated as waste.

In the first desorption step of the process of the present invention, part of the sorbed methane, which is methane that is sorbed by the sorption agent, is desorbed, resulting in a gas stream comprising methane. That is to say, the latter gas stream resulting from the first desorption step comprises methane that is desorbed from the sorption agent. Further, in the present invention, the amount of methane in the gas stream resulting from the first desorption step should be 1 to 99.9% based on the amount of methane in the gas stream that is subjected to the sorption step.

Preferably, in the first desorption step of the process of the present invention, desorption is effected by reducing the pressure. That is to say, the pressure in the first desorption step is lower than the pressure in the sorption step. This is usually referred to as "Pressure Swing Adsorption" (PSA). In the embodiment wherein desorption in the first desorption step is effected by reducing the pressure, the pressure in the sorption step is preferably in the range of from 10 to 20 bar, more preferably 12 to 18 bar.

In a case wherein such relatively low pressure (e.g. at most 20 bar) is used in the sorption step, advantageously no or only part of the third component, being the compound in the gas stream that is subjected to the sorption step for which compound the sorption agent has a lower affinity than for methane and ethylene, is sorbed in addition to methane and ethylene (in the sorption step). Thus, advantageously, in the sorption step of the process of the present invention, a relatively low pressure is applied (e.g. of from 10 to 20 bar as mentioned above). In addition, such low pressure advantageously results in that relatively less compression of the gas stream may be needed. It is especially advantageous that the pressure that may be needed in the sorption step of the process of the present invention may be the same as the pressure in the process from which the gas stream comprising methane and ethylene may originate, such as the pressure in the above-mentioned process of oxidative coupling of methane (OCM). In the latter case, there would be no need at all for any compression of said gas stream in order to carry out said sorption step.

As mentioned above, in the first desorption step of the process of the present invention, part of the sorbed methane is desorbed. In particular, the amount of methane in the gas stream resulting from the first desorption step is 1 to 99.9%, preferably 5 to 99.9%, more preferably 10 to 99.9%, more preferably 15 to 99.9%, most preferably 20 to 99.9%, based on the amount of methane in the gas stream that is subjected to the sorption step. The latter percentage may also be referred to as "methane rejection" (methane not being sorbed, but desorbed or "rejected"). Such "methane rejection" may be varied by varying the pressure and/or the nature of the sorption agent. The amount of methane that is (or remains) sorbed by the sorption agent in the first desorption step may be 0.1 to 99%, preferably 0.1 to 95%, more preferably 0.1 to 90%, more preferably 0.1 to 85%, most preferably 0.1 to 80%, based on the amount of methane in the gas stream that is subjected to the sorption step.

The amount of methane in the gas stream resulting from the first desorption step is at most 99.9%, or at most 99%, or at most 90%, or at most 80%, or at most 70%, or at most 65%, or at most 60%, based on the amount of methane in the gas stream that is subjected to the sorption step. Further, the amount of methane in the gas stream resulting from the first desorption step is at least 1%, or at least 5%, or at least 10%, or at least 15%, or at least 20%, or at least 25% or at least 30%, based on the amount of methane in the gas stream that is subjected to the sorption step. Thus, said amount of methane in the gas stream resulting from the first desorption step is 1 to 99.9% or 30 to 99.9%, or 1 to 60% or 30 to 60%. The amount of methane that is (or remains) sorbed by the sorption agent in the first desorption step may be at least 0.1%, or at least 1%, or at least 10%, or at least 20%, or at least 30%, or at least 35%, or at least 40%, based on the amount of methane in the gas stream that is subjected to the sorption step. Further, the amount of methane that is (or remains) sorbed by the sorption agent in the first desorption step may be at most 99%, or at most 95%, or at most 90%, or at most 85%, or at most 80%, or at most 75%, or at most 70%, based on the amount of methane in the gas stream that is subjected to the sorption step. Thus, said amount of methane that is (or remains) sorbed by the sorption agent in the first desorption step may for example be 0.1 to 99% or 0.1 to 70%, or 40 to 99% or 40 to 70%.

Further, in the embodiment wherein desorption in the first desorption step is effected by reducing the pressure, the pressure in the first desorption step is lower than the pressure in the sorption step. Preferably, the pressure in the first desorption step is in the range of from 5 to 15 bar, more preferably 7 to 13 bar.

The temperature in the first desorption step of the process of the present invention may also vary within wide ranges. Preferably, said temperature is in the range of from 0 to 100° C., more preferably 10 to 80° C., most preferably 25 to 50° C. Advantageously, in the present invention, said first desorption step may be carried out at a non-cryogenic temperature (e.g. of from 0 to 100° C. as mentioned above).

In the second desorption step of the process of the present invention, sorbed compounds, which are compounds that are sorbed by the sorption agent, are desorbed, resulting in a gas stream comprising the desorbed compounds. That is to say, the latter gas stream resulting from the second desorption step comprises compounds that are desorbed from the sorption agent. It is not required that in the second desorption step, all the remaining compounds that are sorbed by the sorption agent are desorbed. These desorbed compounds comprise ethylene and optionally methane. These desorbed compounds comprise both ethylene and methane if for example no rinse step, as discussed hereinbelow, is carried out between the first and second desorption steps.

Preferably, in the second desorption step of the process of the present invention, desorption is effected by reducing the pressure. That is to say, the pressure in the second desorption step is lower than the pressure in the first desorption step. As discussed above, this is usually referred to as "Pressure Swing Adsorption" (PSA). In the embodiment wherein desorption in both the first desorption step and the second desorption step is effected by reducing the pressure, in which case the pressure in the second desorption step is lower than the pressure in the first desorption step and the pressure in the first desorption step in turn is lower than the pressure in the sorption step, the pressure in the sorption step is preferably in the range of from 10 to 20 bar, more preferably 12 to 18 bar, and the pressure in the first desorption step is preferably in the range of from 5 to 15 bar, more preferably 7 to 13 bar.

Further, in the embodiment wherein desorption in the second desorption step is effected by reducing the pressure, the pressure in the second desorption step is lower than the pressure in the first desorption step. Preferably, the pressure in the second desorption step is in the range of from 0.1 to 3 bar, more preferably 0.5 to 2 bar.

The temperature in the second desorption step of the process of the present invention may also vary within wide ranges. Preferably, said temperature is in the range of from 0 to 100° C., more preferably 10 to 80° C., most preferably 25 to 50° C. Advantageously, in the present invention, said second desorption step may be carried out at a non-cryogenic temperature (e.g. of from 0 to 100° C. as mentioned above).

Advantageously, the process of the present invention makes it possible to efficiently separate methane from a gas stream comprising methane, ethylene and the compound for which the sorption agent has a lower affinity than for methane and ethylene (the above-mentioned "third component") at a relatively low pressure (e.g. at most 20 bar in the sorption step and at most 15 bar in the following first desorption step as mentioned above) and at a non-cryogenic temperature (e.g. of from 0 to 100° C. as mentioned above).

Since in the first desorption step of the process of the present invention, also part of the methane is (or remains) sorbed in addition to ethylene, in the second desorption step also methane may be desorbed, resulting in a gas stream comprising ethylene and methane. It may be that in the second desorption step substantially no methane is desorbed, if for example a rinse step, as discussed hereinbelow, is carried out between the first and second desorption steps.

In the embodiment of the process of the present invention, wherein the second desorption step results in desorption of ethylene and methane and in a gas stream comprising ethylene and methane, preferably, further methane is recovered from the gas stream comprising ethylene and methane resulting from the second desorption step. In said embodiment, the process of the present invention comprising the sorption step and first and second desorption steps as described above may additionally comprise a distillation step wherein the gas stream resulting from said second desorption step is distilled. Said distillation step comprises distilling the gas stream comprising ethylene and methane resulting from the second desorption step, said distillation step resulting in a top stream comprising methane and a bottom stream comprising ethylene. Preferably, in said distillation step, the gas stream is distilled at a pressure in the range of from 20 to 40 bar, preferably 23 to 35 bar, and a temperature in the range of from −140 to −50° C., preferably −120 to −70° C. In the present specification, such temperature in a distillation step means the overhead temperature which is the temperature in the condenser at the top of the distillation column.

In said embodiment of the process of the present invention, additionally comprising a distillation step, a distillation column is needed to recover further methane from the gas stream comprising ethylene and methane resulting from the second desorption step. This implies that a compressor is also needed in order to increase the pressure of said gas stream (e.g. to 23 to 35 bar as mentioned above) and further that the temperature should be lowered to a cryogenic temperature (e.g. to −120 to −70° C. as mentioned above), so as to enable separation of methane from ethylene in such "demethanizer" distillation column. However, as is demonstrated in the present Examples, it has surprisingly appeared that advantageously the energy demand, especially the demand for compression and refrigeration energy, even for a process comprising said sorption step, said first desorption step, said second desorption step and said distillation step is significantly lower as compared to a process not comprising said steps but comprising a distillation step wherein the above-mentioned third component and methane are separated from ethylene and a subsequent distillation step wherein methane is separated from said third component, in which latter comparative process no methane is removed from the gas stream comprising methane and ethylene before cryogenic distillation. Thus, the present process is a process that, optionally in combination with said distillation step, enables the recovery of methane from a gas stream comprising methane, ethylene and the compound for which the sorption agent has a lower affinity than for methane and ethylene (said "third component") in a way that is technically feasible, efficient and affordable since the energy demand is surprisingly lower as compared to the prior art process.

Figure 1:
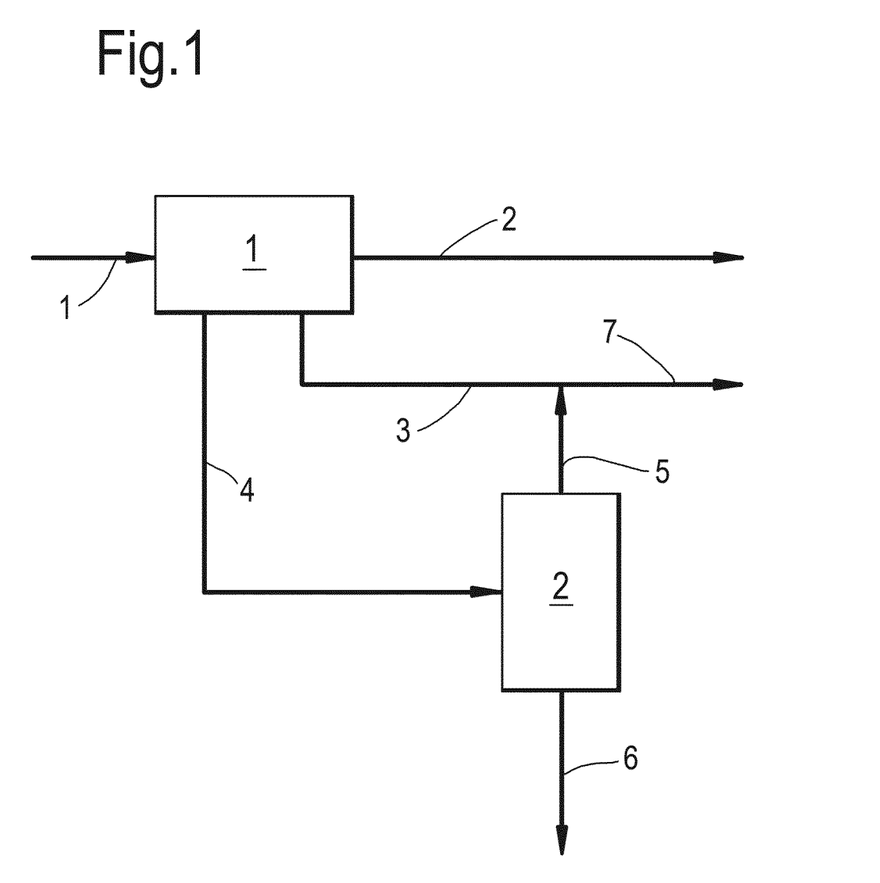
FIG. 1 shows an embodiment of the process of the present invention, wherein the above-mentioned sorption step, first desorption step and second desorption step are followed by a distillation step wherein a gas stream comprising ethylene and methane resulting from said second desorption step is distilled.

An example of an embodiment of the process of the present invention is schematically shown in FIG. 1. In said FIG. 1, a gas stream 1 comprising methane and ethylene is fed to sorption and desorption unit 1 which comprises a sorption agent which has a lower affinity for methane than for ethylene. Further, gas stream 1 also comprises a compound for which the sorption agent has a lower affinity than for methane and ethylene, which latter compound (herein also referred to as the "third component") may for example comprise nitrogen, carbon monoxide, hydrogen or a mixture of two or more of these. The pressure of gas stream 1 is relatively high, for example in the range of from 10 to 20 bar, such that ethylene and methane are sorbed by the sorption agent. A gas stream 2 comprising said third component (originating from gas stream 1) leaves sorption and desorption unit 1, which third component is not sorbed by the sorption agent in sorption and desorption unit 1.

After some time, the feed of gas stream 1 to sorption and desorption unit 1 is stopped and the pressure in said unit is reduced. For example, the pressure in sorption and desorption unit 1 may be reduced to a pressure in the range of from 5 to 15 bar in a case wherein during the sorption step the pressure is in the range of from 10 to 20 bar, as exemplified above. Through such pressure reduction part of the methane that is sorbed by the sorption agent becomes desorbed (first desorption step). A gas stream 3 comprising methane, that is desorbed from the sorption agent, leaves sorption and desorption unit 1.

After some time, the pressure in sorption and desorption unit 1 is further reduced. For example, the pressure in sorption and desorption unit 1 may be reduced to a pressure in the range of from 0.1 to 3 bar in a case wherein during the first sorption step the pressure is in the range of from 5 to 15 bar, as exemplified above. Through such pressure reduction the ethylene and remaining methane that are sorbed by the sorption agent become desorbed (second desorption step). A gas stream 4 comprising ethylene and methane, that are desorbed from the sorption agent, leaves sorption and desorption unit 1, and is then sent to distillation column 2.

Once the desorption is completed, the feed of gas stream 1 to sorption and desorption unit 1 is resumed and the above procedure is repeated.

In distillation column 2, gas stream 4 comprising ethylene and methane is distilled under such pressure and temperature conditions, for example those as described above, that separation between ethylene and methane is effected. That is, a top stream 5 comprising methane and a bottom stream 6 comprising ethylene leave distillation column 2. Finally, top stream 5 comprising methane is combined with gas stream 3 comprising methane resulting in a single stream 7 comprising recovered methane. Said stream 3, stream 5 and/or stream 7, all comprising methane, may advantageously be used (recycled) partially or completely in a process wherein methane is used as a starting material (for further conversion of the recovered methane), for example in the above-mentioned process of oxidative coupling of methane (OCM).

In a particular embodiment of the process of the present invention, the process additionally comprises a rinse step between the first desorption step and the second desorption step. Said rinse step comprises contacting a gas stream, comprising a compound for which the sorption agent has a higher affinity than for methane, with the sorption agent containing sorbed ethylene and methane, resulting in sorption of the compound for which the sorption agent has a higher affinity than for methane by the sorption agent, in desorption of methane from the sorption agent and in a gas stream comprising methane.

In the rinse step of the above-mentioned embodiment of the process of the present invention, the sorption agent containing sorbed ethylene and methane resulting from the above-described first desorption step is contacted with a gas stream comprising a compound for which the sorption agent has a higher affinity than for methane. Since the sorption agent has a lower affinity for methane than for said compound that is present in the gas stream that is used in the rinse step, said rinse step results in sorption of said compound for which the sorption agent has a higher affinity than for methane by the sorption agent, in desorption of methane from the sorption agent and in a gas stream comprising methane. That is to say, the gas stream resulting from the rinse step comprises methane that is desorbed from the sorption agent.

The gas stream that is used in the rinse step of the above-mentioned embodiment of the process of the present invention comprises a compound for which the sorption agent has a higher affinity than for methane. Since, in the process of the present invention, the sorption agent has a lower affinity for methane than for ethylene, the gas stream, comprising a compound for which the sorption agent has a higher affinity than for methane, that is used in the rinse step may comprise ethylene. Preferably, said gas stream that is used in the rinse step contains substantially no methane. Generally, said compound for which the sorption agent has a higher affinity than for methane comprises one or more compounds selected from the group consisting of ethylene, ethane and hydrocarbons having 3 or more carbon atoms. Suitably, said hydrocarbons having 3 or more carbon atoms comprise saturated and unsaturated hydrocarbons having 3 or more carbon atoms, including propane, propylene, butane and butene, and optionally saturated and unsaturated hydrocarbons having 5 or more carbon atoms. Preferably, the gas stream comprising a compound for which the sorption agent has a higher affinity than for methane comprises ethylene, ethane or a mixture of ethylene and ethane, more preferably ethylene.

Thus, in the above-mentioned embodiment of the process of the present invention additionally comprising a rinse step, the sorption agent has a lower affinity for methane than for the compound present in the gas stream that is used in the rinse step. As already discussed above in relation to the sorption step, this means that under the conditions applied in the rinse step, including pressure and temperature which are further defined hereinbelow, said sorption agent has a lower affinity for methane than for said other compound present in the gas stream that is used in the rinse step.

In the above-mentioned embodiment of the process of the present invention additionally comprising a rinse step, the sorbed compounds that are desorbed in the second desorption step are ethylene and said compound for which the sorption agent has a higher affinity than for methane. Thus, the gas stream resulting from the second desorption step in said embodiment comprises ethylene and said compound for which the sorption agent has a higher affinity than for methane.

Preferably, the gas stream to be used during the above-mentioned rinse step is a gas stream that is split off from the gas stream comprising ethylene and the compound for which the sorption agent has a higher affinity than for methane which results from the second desorption step. In that way, advantageously, no external gas stream would be needed to perform the rinse step and a greater process efficiency and integration is thereby achieved. For example, as discussed above, the gas stream comprising a compound for which the sorption agent has a higher affinity than for methane to be used in the rinse step may comprise ethylene, ethane or a mixture of ethylene and ethane, in which case the gas stream which results from the desorption step comprises ethylene or a mixture of ethylene and ethane.

The pressure in the rinse step of the above-mentioned embodiment of the process of the present invention may vary within wide ranges. Preferably, said pressure is higher than atmospheric pressure. More preferably, said pressure is higher than atmospheric pressure and at most 15 bar, more preferably of from 5 to 15 bar, most preferably 7 to 13 bar. Specifically, in a case wherein desorption in the first desorption step and the second desorption step is effected by reducing the pressure, it is preferred that the pressure in the rinse step is the same as the pressure in the first desorption step and higher than the pressure in the second desorption step.

The temperature in the rinse step of the above-mentioned embodiment of the process of the present invention may also vary within wide ranges. Preferably, said temperature is in the range of from 0 to 100° C., more preferably 10 to 80° C., most preferably 25 to 50° C. Advantageously, said rinse step may be carried out at a non-cryogenic temperature (e.g. of from 0 to 100° C. as mentioned above).

Preferably, the gas stream comprising methane, ethylene and the above-mentioned third component, which is the compound for which the sorption agent has a lower affinity than for methane and ethylene, that is subjected to the sorption step of the process of the present invention comprises substantially no water. It is also preferred that said gas stream comprises substantially no hydrogen sulfide.

Within the present specification, by "substantially no" in relation to the amount of a specific component in a gas stream, it is meant an amount which is at most 1,000, preferably at most 500, preferably at most 100, preferably at most 50, more preferably at most 30, more preferably at most 20, and most preferably at most 10 ppmw of the component in question, based on the amount (i.e. weight) of said gas stream.

Further, in an embodiment of the process of the present invention, the gas stream comprising methane, ethylene and said third component (which may be nitrogen, carbon monoxide, hydrogen or a mixture of two or more of these) that is subjected to the sorption step of the process of the present invention additionally comprises components other than said methane, ethylene and third component, such as carbon dioxide, ethane and hydrocarbons having 3 or more carbon atoms.

Suitably, said hydrocarbons having 3 or more carbon atoms comprise saturated and unsaturated hydrocarbons having 3 or more carbon atoms, including propane, propylene, butane and butene, and optionally saturated and unsaturated hydrocarbons having 5 or more carbon atoms.

In the above-mentioned embodiment of the process of the present invention, wherein the gas stream additionally comprises carbon dioxide, ethane and hydrocarbons having 3 or more carbon atoms, said process may be a process, wherein the gas stream that is subjected to the sorption step comprises methane, ethylene, hydrogen, optionally nitrogen, carbon monoxide, carbon dioxide, ethane and hydrocarbons having 3 or more carbon atoms, in which case said process comprises:

a sorption step which comprises contacting said gas stream with a sorption agent which has a lower affinity for hydrogen, nitrogen and carbon monoxide than for methane, ethylene, carbon dioxide, ethane and hydrocarbons having 3 or more carbon atoms, resulting in sorption of hydrocarbons having 3 or more carbon atoms, ethane, ethylene, carbon dioxide and methane by the sorption agent and in a gas stream comprising hydrogen, optionally nitrogen and carbon monoxide;

a first desorption step which comprises desorbing part of the sorbed methane resulting in a gas stream comprising methane in an amount of 1 to 99.9% based on the amount of methane in the gas stream that is subjected to the sorption step; and a second desorption step which comprises desorbing sorbed compounds resulting in a gas stream comprising the desorbed compounds.

Further, preferably, in the above-mentioned embodiment of the process of the present invention, wherein the gas stream additionally comprises components other than methane, ethylene and said third component, the gas stream that is subjected to the sorption step comprises 40 to 90 mol % of methane, 0.5 to 45 mol % of ethylene, 0.01 to 3 mol % of hydrogen, 0 to 80 mol % of nitrogen, 0.1 to 5 mol % of carbon monoxide, 5 to 25 mol % of carbon dioxide, 0.1 to 25 mol % of ethane and 0.5 to 20 mol % of hydrocarbons having 3 or more carbon atoms. Said relative amounts are based on the total amount of the components in the gas stream.

The sorption agents, pressures, temperatures, rinse method (if the optional rinse step as discussed above is also applied) and sorption-desorption method (e.g. PSA) as discussed above also apply to the above-mentioned embodiment of the process of the present invention, wherein the gas stream additionally comprises components other than methane, ethylene and said third component.

Since in the first desorption step of the process of the present invention, also part of the methane is (or remains) sorbed in addition to ethylene, in the second desorption step also methane may be desorbed, resulting in a gas stream comprising carbon dioxide, ethylene, ethane, hydrocarbons having 3 or more carbon atoms and methane in the above-mentioned embodiment. It may be that in the second desorption step substantially no methane is desorbed, if for example a rinse step, as discussed hereinabove, is carried out between the first and second desorption steps. In the latter case, the gas stream resulting from the second desorption step comprises carbon dioxide, ethylene, ethane and hydrocarbons having 3 or more carbon atoms. Therefore, methane is optionally present in the gas stream resulting from the second desorption step in the above-mentioned embodiment.

Preferably, in said embodiment, the process of the present invention additionally comprises a carbon dioxide removal step which comprises removing carbon dioxide from the gas stream resulting from the second desorption step, which latter gas stream comprises carbon dioxide, ethylene, ethane and hydrocarbons having 3 or more carbon atoms and optionally methane, as discussed above, resulting in a gas stream comprising ethylene, ethane and hydrocarbons having 3 or more carbon atoms and optionally methane. In said carbon dioxide removal step, carbon dioxide may be removed by any known method, such as treatment with an amine and then with a caustic agent, such as an aqueous monoethanolamine (MEA) absorption system and aqueous NaOH, respectively, as already mentioned above in the introduction of this specification.

Further, in said embodiment, the process of the present invention may be a process, wherein the gas stream resulting from the carbon dioxide removal step comprises ethylene, ethane, hydrocarbons having 3 or more carbon atoms and methane, said process additionally comprising a distillation step which comprises distilling said gas stream, said distillation step resulting in a top stream comprising methane and a bottom stream comprising ethylene, ethane and hydrocarbons having 3 or more carbon atoms. Preferably, in said distillation step, the gas stream is distilled at a pressure in the range of from 10 to 40 bar, preferably 13 to 35 bar, and a temperature in the range of from −60 to 40° C., preferably −40 to 20° C.

Still further, in said embodiment, the process of the present invention may additionally comprise a distillation step which comprises distilling a gas stream comprising ethylene, ethane and hydrocarbons having 3 or more carbon atoms, which gas stream is a gas stream resulting from the above-mentioned carbon dioxide removal step or the bottom stream resulting from the above-mentioned distillation step, said distillation step resulting in a top stream comprising ethylene and a bottom stream comprising ethane and hydrocarbons having 3 or more carbon atoms. Preferably, in said distillation step, the gas stream is distilled at a pressure in the range of from 10 to 40 bar, preferably 13 to 35 bar, and a temperature in the range of from −60 to 40° C., preferably −40 to 20° C.

In an alternative embodiment, the process of the present invention may additionally comprise a distillation step which comprises distilling the above-mentioned gas stream comprising ethylene, ethane and hydrocarbons having 3 or more carbon atoms, said distillation step resulting in a top stream comprising ethylene and ethane and a bottom stream comprising hydrocarbons having 3 or more carbon atoms. Preferably, in said distillation step, the gas stream is distilled at a pressure in the range of from 10 to 40 bar, preferably 13 to 35 bar, and a temperature in the range of from −60 to 40° C., preferably −40 to 20° C.

Further, preferably, in said alternative embodiment, the process of the present invention additionally comprises a distillation step which comprises distilling the above-mentioned top stream comprising ethylene and ethane, said distillation step resulting in a top stream comprising ethylene and a bottom stream comprising ethane. Preferably, in said distillation step, the top stream is distilled at a pressure in the range of from 10 to 40 bar, preferably 13 to 35 bar, and a temperature in the range of from −60 to 40° C., preferably −40 to 20° C.

Figure 2:
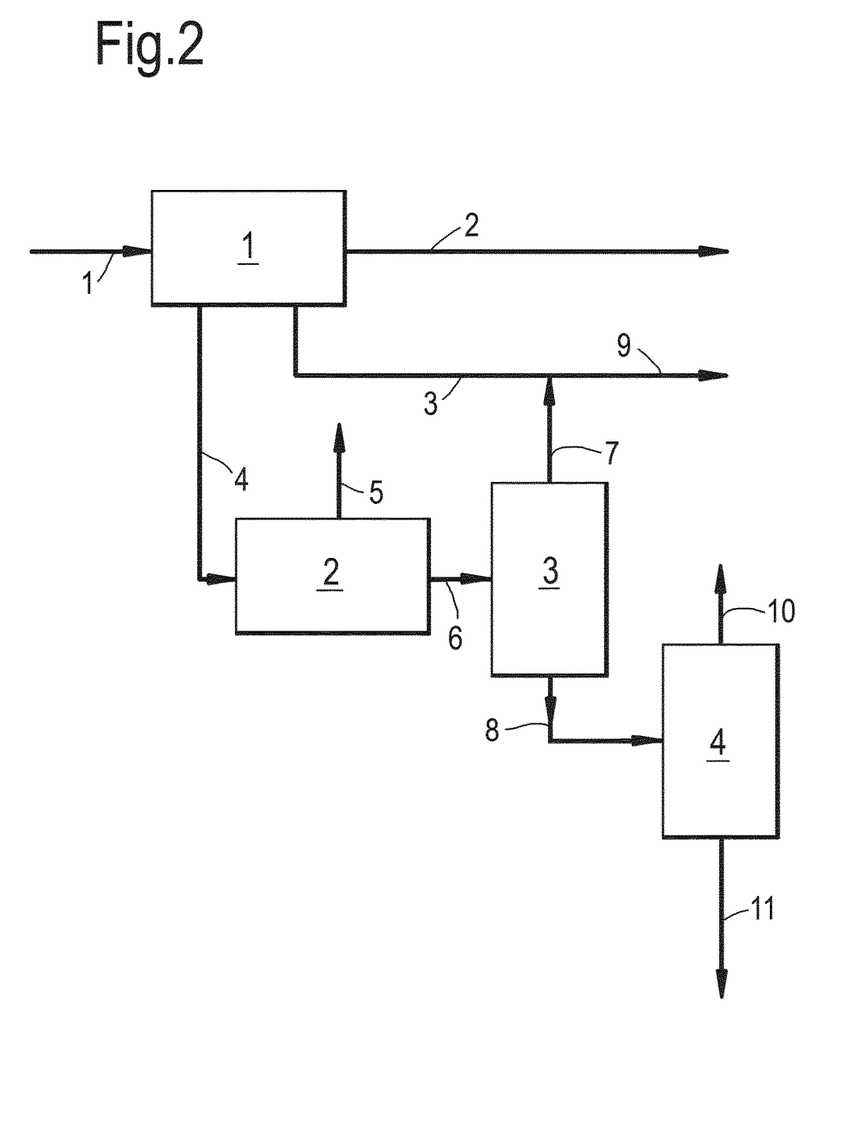
FIG. 2 shows an embodiment of the embodiment shown in FIG. 1, in which the gas stream that is subjected to the sorption step additionally comprises components other than methane, ethylene and one or more light compounds, namely carbon dioxide, ethane and hydrocarbons having 3 or more carbon atoms.

An example of said embodiment of the process of the present invention, wherein the gas stream that is subjected to the sorption step additionally comprises components other than methane, ethylene and said third component is schematically shown in FIG. 2. In said example, the gas stream comprises methane, ethylene, hydrogen, carbon monoxide, nitrogen, carbon dioxide, ethane and hydrocarbons having 3 or more carbon atoms. Hereinafter, the combination of ethylene, ethane and hydrocarbons having 3 or more carbon atoms may also be referred to as hydrocarbons having 2 or more carbon atoms. In said FIG. 2, a gas stream 1 comprising hydrogen, carbon monoxide, nitrogen, carbon dioxide, methane, ethylene, ethane and hydrocarbons having 3 or more carbon atoms is fed to sorption and desorption unit 1 which comprises a sorption agent which has a lower affinity for hydrogen, carbon monoxide and nitrogen than for methane, carbon dioxide and hydrocarbons having 2 or more carbon atoms. The pressure of gas stream 1 is relatively high, for example in the range of from 10 to 20 bar, such that hydrocarbons having 2 or more carbon atoms, carbon dioxide and methane are sorbed by the sorption agent. A gas stream 2 comprising hydrogen, carbon monoxide and nitrogen leaves sorption and desorption unit 1, which hydrogen, carbon monoxide and nitrogen are not sorbed by the sorption agent in sorption and desorption unit 1.

After some time, the feed of gas stream 1 to sorption and desorption unit 1 is stopped and the pressure in said unit is reduced. For example, the pressure in sorption and desorption unit 1 may be reduced to a pressure in the range of from 5 to 15 bar in a case wherein during the sorption step the pressure is in the range of from 10 to 20 bar, as exemplified above. Through such pressure reduction part of the methane that is sorbed by the sorption agent becomes desorbed (first desorption step). A gas stream 3 comprising methane, that is desorbed from the sorption agent, leaves sorption and desorption unit 1.

After some time, the pressure in sorption and desorption unit 1 is further reduced. For example, the pressure in sorption and desorption unit 1 may be reduced to a pressure in the range of from 0.1 to 3 bar in a case wherein during the first sorption step the pressure is in the range of from 5 to 15 bar, as exemplified above. Through such pressure reduction the carbon dioxide, hydrocarbons having 2 or more carbon atoms and remaining methane that are sorbed by the sorption agent become desorbed (second desorption step). A gas stream 4 comprising carbon dioxide, hydrocarbons having 2 or more carbon atoms and methane, that are desorbed from the sorption agent, leaves sorption and desorption unit 1, and is then sent to carbon dioxide removal unit 2.

Once the desorption is completed, the feed of gas stream 1 to sorption and desorption unit 1 is resumed and the above procedure is repeated.

In carbon dioxide removal unit 2, carbon dioxide is removed, via stream 5, from gas stream 4 comprising carbon dioxide, hydrocarbons having 2 or more carbon atoms and methane, in a way as exemplified above. A gas stream 6 comprising hydrocarbons having 2 or more carbon atoms and methane leaves carbon dioxide removal unit 2 and is sent to distillation column 3.

In distillation column 3, gas stream 6 comprising hydrocarbons having 2 or more carbon atoms and methane is distilled under such pressure and temperature conditions, for example those as described above, that separation between on the one hand methane and on the other hand hydrocarbons having 2 or more carbon atoms is effected. That is, a top stream 7 comprising methane and a bottom stream 8 comprising hydrocarbons having 2 or more carbon atoms leave distillation column 3. Bottom stream 8 is sent to distillation column 4.

In distillation column 4, bottom stream 8 comprising hydrocarbons having 2 or more carbon atoms is distilled under such pressure and temperature conditions, for example those as described above, that separation between on the one hand ethylene and on the other hand ethane and hydrocarbons having 3 or more carbon atoms is effected. That is, a top stream 10 comprising ethylene and a bottom stream 11 comprising ethane and hydrocarbons having 3 or more carbon atoms leave distillation column 4.

Finally, top stream 7 comprising methane is combined with stream 3 comprising methane resulting in a single stream 9 comprising recovered methane. Said stream 3, stream 7 and/or stream 9, all comprising methane, may advantageously be used (recycled) partially or completely in a process wherein methane is used as a starting material (for further conversion of the recovered methane), for example in the above-mentioned process of oxidative coupling of methane (OCM).

The invention is further illustrated by the following Examples.

EXAMPLES AND COMPARATIVE EXAMPLE

In the Examples exemplifying the invention, the set-up as shown in FIG. 1 is used to recover methane from a gas stream comprising methane, ethylene and nitrogen, said set-up comprising sorption and desorption unit 1 and distillation column 2, as described in the description preceding these Examples.

In the Comparative Example exemplifying a prior art process, two distillation columns are used to recover methane from a gas stream comprising methane, ethylene and nitrogen.

In the Examples, a gas stream 1 comprising 70 wt. % of methane, 10 wt. % of ethylene and 20 wt. % of nitrogen is fed at a temperature of 43° C. and a pressure of 9.8 bar to sorption and desorption unit 1 which comprises a sorption agent, which sorption agent has a lower affinity for methane than for ethylene and which sorption agent has an affinity for nitrogen which is lower than its affinity for methane and ethylene. Ethylene and methane from gas stream 1 are sorbed by the sorption agent. A gas stream 2 comprising 81 wt. % of nitrogen leaves sorption and desorption unit 1, which nitrogen is not sorbed by the sorption agent in sorption and desorption unit 1. Gas stream 2 is produced at the same temperature and pressure as gas stream 1 is fed to sorption and desorption unit 1, that is to say 43° C. and 9.8 bar, respectively.

After some time, the feed of gas stream 1 to sorption and desorption unit 1 is stopped and the pressure in sorption and desorption unit 1 is reduced from 9.8 bar to 1 bar, thereby inducing the first desorption step of the process of the present invention. Part of the sorbed methane (60 or 90% of the methane from gas stream 1) subsequently becomes desorbed from the sorption agent and leaves sorption and desorption unit 1 via gas stream 3 at a temperature of 43° C. and a pressure of 1 bar. Gas stream 3 comprises 95 wt. % of methane. The percentage of methane which leaves sorption and desorption unit 1 via gas stream 3 (which methane is desorbed) is called the "methane rejection" and is based on the amount of methane as fed to sorption and desorption unit 1 via gas stream 1, and is 60 or 90%, respectively, in the "PSA60" and "PSA90" cases, respectively.

Further, after some time, the pressure in sorption and desorption unit 1 is further reduced from 9.8 bar to 1 bar, thereby inducing the second desorption step of the process of the present invention. The sorbed components (ethylene and 40 or 10% of the methane from gas stream 1) subsequently become desorbed from the sorption agent and leave sorption and desorption unit 1 via gas stream 4 at a temperature of 43° C. and a pressure of 1 bar. In both cases ("PSA60" and "PSA90", as described above in relation to the first desorption step), gas stream 4 is advantageously enriched in ethylene as compared to gas stream 1. In Table 1 below, the composition of gas stream 4 is shown for both cases in the Examples. In said Table 1, the "methane rejection" refers to the methane rejection in the first desorption step (as described above), whereas gas stream 4 is produced in this second desorption step.

TABLE 1

|  |  | Methane (wt. %) | Ethylene (wt. %) | Nitrogen (wt. %) |
|---|---|---|---|---|
|  | Gas stream 1 | 70 | 10 | 20 |
| Gas stream 4 | Methane rejection |  |  |  |
| PSA60 | 60% | 74 | 26 | 0 |
| PSA90 | 90% | 41 | 59 | 0 |

Gas stream 4 is then recompressed to 9.8 bar in a first compressor, further compressed to 32.0 bar in a second compressor and finally cooled to −69° C. before it enters distillation column 2 which is a column having 22 theoretical stages. In distillation column 2, the following 2 streams are separated: a top stream comprising 99.7 wt. % of methane at an (overhead) temperature of −95° C. and a pressure of 31.0 bar (top stream 5) and a bottom stream comprising 99.9+ wt. % of ethylene at a temperature of −5° C. and a pressure of 31.2 bar (bottom stream 6).

In Table 2 below, the reflux ratios and the distillate-to-feed ratios needed to achieve the above separation for the "PSA60" and "PSA90" cases are mentioned. By said "reflux ratio", reference is made to the molar ratio of the molar flow rate of the "reflux stream", which is that part of the stream that leaves the condenser at the top of the distillation column which is sent back to that column, divided by the molar flow rate of the "distillate", which is that part of the stream that leaves the condenser at the top of the distillation column which is not sent back to that column. By said "distillate-to-feed ratio", reference is made to the molar ratio of the molar flow rate of said "distillate" divided by the molar flow rate of the feedstream that is fed to that column (the "feed") which in this case is gas stream 4 having the composition as shown in Table 1 above.

TABLE 2

|  | Reflux ratio | Distillate-to-feed ratio |
|---|---|---|
| PSA60 | 1.8 | 0.74 |
| PSA90 | 3.8 | 0.41 |

Finally, said top stream 5 comprising methane is combined with gas stream 3 comprising methane resulting in a single stream 7 comprising recovered methane.

As already mentioned above, in the Comparative Example ("base case"), two distillation columns (and not sorption and desorption unit 1 as shown in FIG. 1) are used to recover methane from a gas stream comprising methane, ethylene and nitrogen. Said gas stream is the same as gas stream 1, that is to say a gas stream comprising 70 wt. % of methane, 10 wt. % of ethylene and 20 wt. % of nitrogen. In the Comparative Example, said gas stream is sent to a first distillation column which is the same as above-mentioned distillation column 2. Further reference is made to the above discussion of characteristics and operation of distillation column 2 which also apply to this Comparative Example. In relation to this first distillation column as used in this base case, the reflux ratio and the distillate-to-feed ratio are 0.62 and 0.90, respectively. In this first distillation column, the following 2 streams are separated: a top stream comprising methane and nitrogen and a bottom stream comprising 99.3 wt. % of ethylene.

In a second step of the Comparative Example, said top stream comprising methane and nitrogen is cooled to −107° C. before it enters a second distillation column which is a column having 19 theoretical stages. In this second distillation column, the reflux ratio and the distillate-to-feed ratio are 2.10 and 0.20, and the following 2 streams are separated: a top stream comprising 73 wt. % of nitrogen at an (overhead) temperature of −122° C. and a pressure of 30 bar and a bottom stream comprising 95.5 wt. % of methane at a temperature of −98° C. and a pressure of 30.3 bar.

In Table 3 below, the compression and refrigeration energy needed to recover methane from the gas stream comprising methane, ethylene and nitrogen is included for all of the above-discussed cases, that is to say both the comparative "base case" (Comparative Example) and the cases of the invention which are the "PSA60" and "PSA90"

cases (Examples). Said energy is expressed as kilowatt hour ("kWh"; 1 kWh=3.6 megajoules) per kilogram (kg) of ethylene.

TABLE 3

| Case | Configuration | kWh/kg of ethylene |
| --- | --- | --- |
| base case | 2 distillations (comparative) | 1.381 |
| PSA60 | PSA + distillation | 0.955 |
| PSA90 | PSA + distillation | 0.482 |

From Table 3 above, it surprisingly appears that the energy needed to recover methane from the gas stream comprising methane, ethylene and nitrogen is advantageously lowest in case the process of the present invention is carried out. That is, in the "PSA60" and "PSA90" cases which exemplify the sorption and desorption process of the present invention, the energy needed to recover said methane, is advantageously lower than the energy needed to effect the same in the "base case" in which latter case such sorption and desorption process is not applied but two distillation steps are performed.

Thus, surprisingly, this advantageous different energy effect obtained with the sorption and desorption process of the present invention, as compared to the prior art process wherein two distillation steps are performed, is even obtained in cases where said sorption and desorption process is followed by a distillation step to recover further methane from gas stream 4, as in the "PSA60" and "PSA90" cases.

That which is claimed is:

1. A process for recovering methane from a gas stream comprising methane and ethylene, comprising:
    a sorption step which comprises contacting the gas stream comprising methane and ethylene with a sorption agent which has a lower affinity for methane than for ethylene, wherein the gas stream comprising methane and ethylene also comprises a compound for which the sorption agent has a lower affinity than for methane and ethylene, resulting in sorption of ethylene and methane by the sorption agent and in a gas stream comprising the compound for which the sorption agent has a lower affinity than for methane and ethylene;
    a first desorption step which comprises desorbing part of the sorbed methane resulting in a gas stream comprising methane in an amount of 1 to 99.9% based on the amount of methane in the gas stream that is subjected to the sorption step;
    a second desorption step which comprises desorbing sorbed compounds resulting in a gas stream comprising the desorbed compounds; and
    a rinse step between the first desorption step and the second desorption step, which rinse step comprises contacting a gas stream, comprising a compound for which the sorption agent has a higher affinity than for methane, with the sorption agent containing sorbed ethylene and methane, resulting in sorption of the compound for which the sorption agent has a higher affinity than for methane by the sorption agent, in desorption of methane from the sorption agent and in a gas stream comprising methane.

2. The process according to claim 1, wherein the compound for which the sorption agent has a lower affinity than for methane and ethylene is nitrogen, carbon monoxide, hydrogen or a mixture of two or more of these.

3. The process according to claim 1, wherein the gas stream that is subjected to the sorption step comprises 50 to 99 mol % of methane, 1 to 50 mol % of ethylene and 0.1 to 90 mol % of the compound for which the sorption agent has a lower affinity than for methane and ethylene.

4. The process according to claim 1, wherein desorption in the first desorption step and the second desorption step is effected by reducing the pressure.

5. The process according to claim 4, wherein the pressure in the sorption step is in the range of from 10 to 20 bar, the pressure in the first desorption step is in the range of from 5 to 15 bar, and the pressure in the second desorption step is in the range of from 0.1 to 3 bar.

6. The process according to claim 1, wherein the second desorption step results in a gas stream comprising ethylene and methane, which process additionally comprises a distillation step which comprises distilling the gas stream comprising ethylene and methane resulting from the second desorption step, said distillation step resulting in a top stream comprising methane and a bottom stream comprising ethylene.

7. The process according to claim 1, wherein the compound for which the sorption agent has a higher affinity than for methane comprises one or more compounds selected from the group consisting of ethylene, ethane and hydrocarbons having 3 or more carbon atoms.

8. The process according to claim 7, wherein the gas stream comprising a compound for which the sorption agent has a higher affinity than for methane comprises ethylene, ethane or a mixture of ethylene and ethane.

9. The process according to claim 1, wherein desorption in the first desorption step and the second desorption step is effected by reducing the pressure, and the pressure in the rinse step is in the range of from 5 to 15 bar.

10. The process according to claim 1, wherein the gas stream that is subjected to the sorption step further comprises hydrogen, optionally nitrogen, carbon monoxide, carbon dioxide, ethane and hydrocarbons having 3 or more carbon atoms,
    wherein the sorption step comprises contacting said gas stream with a sorption agent which has a lower affinity for hydrogen, nitrogen and carbon monoxide than for methane, ethylene, carbon dioxide, ethane and hydrocarbons having 3 or more carbon atoms, resulting in sorption of hydrocarbons having 3 or more carbon atoms, ethane, ethylene, carbon dioxide and methane by the sorption agent and in a gas stream comprising hydrogen, optionally nitrogen and carbon monoxide.

11. The process according to claim 10, wherein the gas stream that is subjected to the sorption step comprises 40 to 90 mol % of methane, 0.5 to 45 mol % of ethylene, 0.01 to 3 mol % of hydrogen, 0 to 80 mol % of nitrogen, 0.1 to 5 mol % of carbon monoxide, 5 to 25 mol % of carbon dioxide, 0.1 to 25 mol % of ethane and 0.5 to 20 mol % of hydrocarbons having 3 or more carbon atoms.

12. The process according to claim 10, additionally comprising a carbon dioxide removal step which comprises removing carbon dioxide from the gas stream resulting from the second desorption step, resulting in a gas stream comprising ethylene, ethane and hydrocarbons having 3 or more carbon atoms and optionally methane.

13. The process according to claim 12, wherein the gas stream resulting from the carbon dioxide removal step comprises ethylene, ethane, hydrocarbons having 3 or more carbon atoms and methane, additionally comprising a distillation step which comprises distilling said gas stream, said distillation step resulting in a top stream comprising methane and a bottom stream comprising ethylene, ethane and hydrocarbons having 3 or more carbon atoms.

14. The process according to claim 12, additionally comprising a distillation step which comprises distilling a gas stream comprising ethylene, ethane and hydrocarbons having 3 or more carbon atoms, which gas stream is a gas stream resulting from the carbon dioxide removal step of claim 12 or the bottom stream resulting from the distillation step of claim 13, said distillation step resulting in a top stream comprising ethylene and a bottom stream comprising ethane and hydrocarbons having 3 or more carbon atoms.

* * * * *